United States Patent [19]  
Broughton et al.

[11] 4,039,544  
[45] Aug. 2, 1977

[54] AZAPURINONES

[75] Inventors: Barbara Joyce Broughton, Croydon; Bryan John Large, Ilkley; Stuart Malcolm Marshall, Stanford-Le-Hope; David Lord Pain, Upminster; Kenneth Robert Harry Wooldridge, Brentwood, all of England

[73] Assignee: May & Baker Limited, England

[21] Appl. No.: 680,444

[22] Filed: Apr. 26, 1976

Related U.S. Application Data

[63] Continuation-in-part of Ser. No. 364,425, May 29, 1973, Pat. No. 3,987,160, which is a continuation of Ser. No. 207,986, Dec. 14, 1971, Pat. No. 3,819,631.

[30] Foreign Application Priority Data

| Dec. 15, 1970 | United Kingdom | 59552/70 |
| Dec. 15, 1970 | United Kingdom | 59556/70 |
| Oct. 26, 1971 | United Kingdom | 49756/71 |
| Nov. 17, 1971 | United Kingdom | 53457/71 |
| Apr. 28, 1975 | United Kingdom | 17573/75 |
| June 2, 1975 | United Kingdom | 23785/75 |

[51] Int. Cl.$^2$ .......................................... C07D 487/04  
[52] U.S. Cl. ........................ 260/256.4 F; 260/256.4 C; 260/256.5 R; 424/45; 424/251  
[58] Field of Search ................. 260/256.4 F; 424/251, 424/45

[56] References Cited

U.S. PATENT DOCUMENTS

| 2,407,204 | 9/1946 | English et al. | ................ 260/256.4 F |
| 3,987,160 | 10/1976 | Broughton et al | .................... 424/45 |

Primary Examiner—Donald G. Daus  
Assistant Examiner—James H. Turnipseed  
Attorney, Agent, or Firm—Stevens, Davis, Miller & Mosher

[57] ABSTRACT

The invention provides certain novel 8-azapurin-6-one derivatives substituted in the 2-position by a substituted phenyl group, preferably carrying an alkoxy in the 2-position, which possess valuable pharmacological properties especially in the treatment of respiratory disorders manifested by the interaction of tissue-fixed antibodies with specific antigens.

13 Claims, No Drawings

AZAPURINONES

This application is a continuation-in-part of our application Ser. No. 364,425 filed May 29th 1973, now U.S. Pat. No. 3,987,160, itself a continuation of our application Ser. No. 207,986, filed Dec. 14th 1971, now U.S. Pat. No. 3,819,631.

This invention relates to new therapeutically useful 8-azapurin-6-one derivatives, to their preparation, to pharmaceutical compositions containing them, and to their use.

In the specifications of our U.S. Pat. No. 3,819,631 patented 25th June 1974 and of our application Ser. No. 364,425, filed 29th May 1973, the disclosures of which are incorporated herein by specific reference, we have described the class of new 8-azapurin-6-one derivatives represented by the general formula:

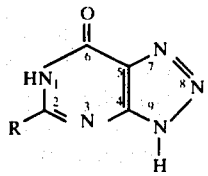

I wherein R represents a phenyl or naphthyl group, which may optionally carry one or more (preferably at most three) substituents selected from halogen (preferably fluorine, chlorine or bromine) atoms and hydroxy, alkyl, phenylalkyl, alkoxy, alkenyloxy, alkynyloxy, alkoxyalkoxy, phenoxy, aralkoxy (e.g. phenylalkoxy), alkylthio, hydroxyalkyl, nitro, alkylsulphonyl, alkanoyl, alkoxycarbonyl, amino, trifluoromethyl and methylenedioxy groups and amino groups substituted by one or two groups selected from alkyl, phenyl, alkanoyl, alkylsulphonyl and arylsulphonyl (e.g. phenylsulphonyl) groups, or R represents a straight- or branched-chain alkenyl or alkynyl group containing from 2 to 6 carbon atoms, a cycloalkyl group containing from 3 to 8 carbon atoms (e.g. cyclohexyl), a straight- or branched-chain alkyl group containing from 2 to 10 carbon atoms (preferably isopropyl, butyl or isobutyl), or a straight- or branched-chain alkyl group containing from 1 to 10 carbon atoms (preferably methyl or ethyl) carrying one or more (preferably at most two) substituents selected from halogen atoms, hydroxy groups, cycloalkyl groups containing from 3 to 8 carbon atoms (preferably cyclohexyl), straight- or branched-chain alkoxy groups containing from 1 to 6 carbon atoms, and phenyl groups optionally carrying one or more (preferably at most two) substituents selected from halogen atoms and straight- or branched-chain alkyl and alkoxy groups containing from 1 to 6 carbon atoms, hydroxy groups, and phenylalkoxy (e.g. benzyloxy) groups in which the alkoxy moiety contains 1 to 6 carbon atoms, and pharmaceutically acceptable salts thereof.

In those specifications it is stated that, when R represents a substituted phenyl or substituted naphthyl group, alkyl groups and alkyl portions of phenylalkyl, alkylthio, aralkoxy, alkanoyl, alkylsulphonyl, hydroxyalkyl and alkoxycarbonyl substituents contain from 1 to 6 carbon atoms, each alkyl portion of an alkoxyalkoxy substituent contains from 1 to 6 carbon atoms; alkoxy substituents contain from 1 to 10 carbon atoms; alkenyloxy and alkynyloxy substituents contain 2 to 10 carbon atoms, and alkyl and alkanoyl groups on amino substituents contain from 1 to 6 carbon atoms; phenoxy substituents, and phenyl groups on amino substituents may carry one or more substituents selected from halogen (e.g. fluorine, chlorine or bromine) atoms, and alkyl and alkoxy groups containing from 1 to 6 carbon atoms; aryl (e.g. phenyl) portions of aralkoxy substituents may carry one or more substituents selected from halogen (e.g. fluorine, chlorine or bromine) atoms, alkyl and alkoxy groups containing from 1 to 6 carbon atoms and nitro groups; and aryl (e.g. phenyl) portions of arylsulphonyl groups on amino substituents may carry one or more alkyl groups containing from 1 to 6 carbon atoms (e.g. methyl). It is further stated that the carbon atoms in the alkyl, alkoxy, alkanoyl, alkenyloxy and alkynyloxy groups or moieties may be in a straight- or branched-chain.

It is pointed out in our above-mentioned specifications that the compounds of formula I exhibit tautomerism such that each of the hydrogen atoms depicted as residing on the nitrogen atoms in the 1- and 9-positions may reside on any of the nitrogen atoms in the 1-, 3-, 7-, 8- and 9-positions or on the oxygen atom connected to the carbon atom in the 6-position, and that all the forms thus described may be present to a greater or lesser degree and are in a state of dynamic equilibrium with each other. Furthermore, in certain cases the substituent R contributes to optical and/or stereoisomerism. All such forms are embraced by the invention described in our aforementioned specifications.

The 8-azapurin-6-one derivatives of general formula I described in our aforementioned specifications possess valuable pharmacological properties, in particular properties of value in the treatment of respiratory disorders manifested by the interaction of tissue-fixed antibodies with specific antigens, such as allergic bronchial asthma.

As a result of further research and experimentation it has now been found that a new class of compounds, some of which fall within the scope of general formula I but have not been specifically described, and others of which are new compounds closely related to the compounds of general formula I, exhibit valuable pharmacological properties similar to those of the 8-azapurin-6-one derivatives specifically described in our aforementioned specifications with, in some aspects of their activities, a marked improvement over the known compounds.

The new compounds within general formula I which have not been specifically described are those wherein, in general formula I, R represents a phenyl group carrying one or more alkoxycarbonyl, alkylthio or alkylsulphonyl groups as well as carrying one or more other substituents as hereinbefore described.

Among the new compounds within general formula I which display the said marked improvement in properties there are:

8-aza-2-(2-propoxy-5-propylsulphonylphenyl)purin-6-one,
8-aza-2-(2-propoxy-5-methylsulphonylphenyl)purin-6-one,
8-aza-2-(2-propoxy-5-t-butylsulphonylphenyl)purin-6-one,
8-aza-2-(2-propoxy-5-isopropylsulphonylphenyl)purin-6-one,
8-aza-2-(2-propoxy-5-isobutylsulphonylphenyl)purin-6-one, 8-aza-2-(2-propoxy-5-t-butylthiophenyl)purin-6-one,
8-aza-2-(5-ethoxycarbonyl-2-propoxyphenyl)purin-6-one,
8-aza-2-(5-methoxycarbonyl-2-propoxyphenyl)purin-6-one, and
8-aza-2-(5-butoxycarbonyl-2-propoxyphenyl)purin-6-one.

The new compounds of the present invention, which are closely related to the compounds of general formula I, are 8-azapurin-6-one derivatives having a phenyl substituent attached to the 2-position, the phenyl ring carrying an alkylsulphinyl substituent and one or more other substituents such as those which may be carried by the phenyl group represented by the symbol R in formula I. A preferred example of such a novel compound is 8-aza-2-(2-propoxy-5-t-butylsulphinylphenyl)-purin-6-one.

The present invention accordingly provides 8-azapurin-6-one derivatives of the general formula:

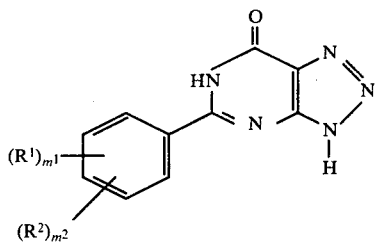

II wherein $R^1$ represents an alkylthio, alkylsulphinyl, alkylsulphonyl or alkoxycarbonyl group, $R^2$ represents a halogen (preferably fluorine, chlorine or bromine) atom, a hydroxy, alkyl, phenylalkyl, alkoxy, alkenyloxy, alkynyloxy, alkoxyalkoxy, phenoxy, aralkoxy (e.g. phenylalkoxy), hydroxyalkyl, alkanoyl, trifluoromethyl or methylenedioxy group or an amino group substituted by two groups selected from alkyl, phenyl, alkanoyl, alkylsulphonyl and arylsulphonyl (e.g. phenylsulphonyl) groups or by one group selected from alkanoyl, alkylsulphonyl and arylsulphonyl (e.g. phenylsulphonyl) groups, $m^1$ represents an integer from 1 to 4 (preferably 1) and $m^2$ represents an integer from 1 to 4 (preferably 1) the sum of $m^1 + m^2$ being not greater than 5 (preferably 2), and pharmaceutically acceptable salts thereof, which possess valuable pharmacological properties similar to the properites of the known compounds of general formula I, but markedly superior to them in some aspects.

When the symbol $m^1$ represents an integer greater than one the substituents represented by the symbol $R^1$ may be different but are preferably identical. When the symbol $m^2$ represents an integer greater than one the substituents represented by the symbol $R^2$ may be identical or different.

In this specification it is to be understood that, unless otherwise specified, alkyl groups and alkyl portions of alkylthio, alkylsulphinyl, alkylsulphonyl, alkoxycarbonyl, phenylalkyl, aralkoxy, alkanoyl and hydroxyalkyl groups contain from 1 to 6 carbon atoms, each alkyl portion of an alkoxyalkoxy substituent contains from 1 to 6 carbon atoms; alkoxy groups contain from 1 to 10 carbon atoms; alkenyloxy and alkynyloxy substituents contain from 2 to 10 carbon atoms; phenoxy groups, and phenyl groups on amino substituents may carry one or more substituents selected from halogen (e.g. fluorine, chlorine or bromine) atoms, and alkyl and alkoxy groups containing from 1 to 6 carbon atoms; aryl (e.g. phenyl) portions of aralkoxy substituents may carry one or more substituents selected from halogen (e.g. fluorine, chlorine or bromine) atoms, and alkyl and alkoxy groups containing from 1 to 6 carbon atoms; and aryl (e.g. phenyl) portions of arylsulphonyl groups on amino substituents may carry one or more alkyl groups containing from 1 to 6 carbon atoms (e.g. methyl). The carbon atoms in the alkyl, alkoxy, alkanoyl, alkenyloxy and alkynyloxy groups or moieties may be in a straight- or branched-chain.

It will be appreciated that compounds of general formula II may exhibit tautomerism as described in our aforementioned specifications in relation to compounds of general formula I.

Compounds of formula II wherein $R^2$ represents an alkoxy group, particularly an alkoxy group containing from 1 to 4 (e.g. 3) carbon atoms, are of especial importance.

Compounds of formula II wherein $R^2$ represents a group in the position on the phenyl ring adjacent to the position by which that ring is attached to the azapurinone ring are particularly preferred.

A group of compounds of formula II of unusual interest are those within the general formula:

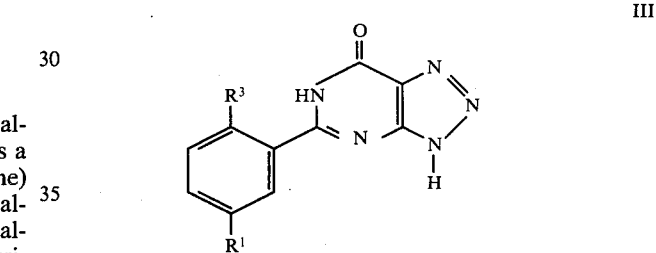

III

[wherein $R^3$ represents a straight- or branched-chain alkoxy group containing from 1 to 4 carbon atoms, e.g. a propoxy group, and $R^1$ is as hereinbefore defined, e.g. a t-butylthio, t-butylsulphinyl, methylsulphonyl, propylsulphonyl, isopropylsulphonyl, isobutylsulphonyl, t-butylsulphonyl, methoxycarbonyl, ethoxycarbonyl or butoxycarbonyl group] and pharmaceutically acceptable salts thereof.

As hereinbefore mentioned, it has been found as a result of research and experimentation that the hitherto undescribed compounds of formula II exhibit valuable pharmacological properties similar to those of the previously described 8-azapurin-6-one derivatives of formula I with, in some aspects of their properties, a marked improvement.

For example, the new compounds of general formula II suppress the passive cutaneous anaphylactic (PCA) reaction resulting from combination of tissue-fixed reaginic antibodies with the appropriate antigenic material (termed reagin-allergen combination) in tests carried out in a similar manner to those described in our aforementioned specifications.

The new compounds, when given intravenously to rats just before injection of allergen at doses of, for example, 0.0001–2.0 mg./kg. were able to prevent the development of the reaction.

In our aforementioned specifications it is stated that 8-aza-2-(2-propoxyphenyl)purin-6-one is one of the two most important compounds of general formula I.

The compounds of the present invention have been directly compared with 8-aza-2-(2-propoxyphenyl)purin-6-one (hereinafter referred to as reference compound "A") in the abovementioned pharmacological test and were found to be between 2 and 20 times as active as that compound. For example, the following compounds have the stated activities relative to the reference compound "A":

| | |
|---|---|
| 8-aza-2-(2-propoxy-5-methylsulphonylphenyl)purin-6-one | 5 × A |
| 8-aza-2-(2-propoxy-5-propylsulphonylphenyl)purin-6-one | 20 × A |
| 8-aza-2-(2-propoxy-5-isopropylsulphonylphenyl)purin-6-one | 10 × A |
| 8-aza-2-(2-propoxy-5-isobutylsulphonylphenyl)purin-6-one | 5 × A |
| 8-aza-2-(2-propoxy-5-t-butylsulphonylphenyl)purin-6-one | 2 × A |
| 8-aza-2-(5-methoxycarbonyl-2-propoxyphenyl)purin-6-one | 2 × A |
| 8-aza-2-(5-methoxycarbonyl)-2-propoxyphenyl)purin-6-one | 2 × A |
| 8-aza-2-(5-butoxycarbonyl-2-propoxyphenyl)purin-6-one | 2 × A |

In our aforementioned specifications there are described certain compounds of general formula I in which R represents an alkylsulphonylphenyl or alkylthiophenyl group. These compounds have the following activities in the above-mentioned test, compared with reference compound A:

| | |
|---|---|
| 8-aza-2-(2-methylthiophenyl)purin-6-one | 0.05 × A |
| 8-aza-2-(3-methylthiophenyl)purin-6-one | 0.02 × A |
| 8-aza-2-(2-methylsulphonylphenyl)purin-6-one | 0.0005 × A |
| 8-aza-2-(4-methylsulphonylphenyl)purin-6-one | 0.02 × A |
| 8-aza-2-(2-butylsulphonylphenyl)purin-6-one | 0.0005 × A |

The compounds of the present invention possess other advantages over reference compound A. For example, 8-aza-2-(2-propoxy-5-propylsulphonylphenyl)purin-6-one, which is an especially important compound of the present invention, does not induce emesis in dogs even when administered orally at a dose of 200 mg./kg. animal body weight, whereas reference compound A does induce emesis in dogs when administered orally a a dose of 100 mg./kg. animal body weight.

In a further pharmacological test in vitro the new compounds of the present invention inhibit the release of histamine and of SRS-A ("slow reacting substance of anaphylaxis"; Brocklehurst; 1962) from passively sensitised human lung tissue incubated with antigen. In the method used, macroscopically normal lung tissue obtained from surgical operations was incubated overnight at room temperature in serum (diluted with Tyrode's solution) obtained from asthmatic patients sensitive to the house-mite Dermatophagoides farinae. At the end of this sensitisation period the tissue was washed free from serum (by means of Tyrode's solution) and divided into aliquots. The aliquots were suspended in Tyrode'ssolution at 37° C. Each aliquot was then treated either with a solution of one of the new compounds in Tyrode's solution, or with Tyrode's solution alone as a control. Immediately thereafter, each mixture was treated with an antigen consisting of an extract of Dermatophagoides farinae as a challenge, and the mixture gently shaken at 37° C. for 20 minutes. The percentages of the total tissue histamine, and of the SRS-A, released by antigen challenge in the presence or absence of the new compounds, and hence the precentage inhibitions of histamine release, and of SRS-A release, caused by the new compounds, were then determined, in comparison with the percentage inhibitions caused by reference compound A. 8-Aza-2-(2-propoxy-5-propylsulphonylphenyl)purin-6-one was found thereby to be approximately equiactive with reference compound A in the inhibition of histamine release, but was found to be between 1.5 and 6 times as active as reference compound A in the inhibition of SRS-A.

The unexpected test results described above demonstrate the surprising advantage of the new compounds of the present invention over the hitherto disclosed compounds of general formula I.

The compounds of general formula II (especially those wherein $R^1$ represents an alkylthio, alkylsulphonyl or alkoxycarbonyl group) may be prepared by the methods described in our aforementioned specifications for the preparation of compounds of general formula I.

Thus, compounds of general formula II wherein the various symbols are as hereinbefore defined may be prepared from compounds of the genral formulae:

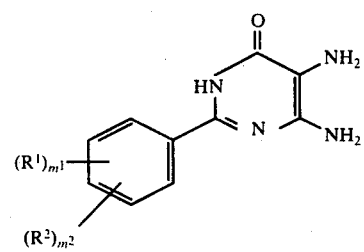

IV wherein $R^1$, $R^2$, $m^1$ and $m^2$ are as hereinbefore defined) by the action of a source of nitrous acid, for example a nitrite of an alkali metal, e.g. sodium nitrite or potassium nitrite, together with an acid, for example dilute aqueous hydrochloric acid or acetic acid, preferably as the reaction medium, at a temperature near or below the ambient temperature, for example between 0° and 30° C.

Compounds of formula IV may be prepared, for example, by the reduction of compounds of the general formula:

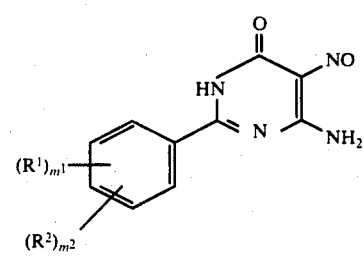

V (wherein $R^1$, $R^2$, $m^1$ and $m^2$ are as hereinbefore defined) with suitable reducing agents, for example sodium dithionite in water or an aqueous lower alkanol, e.g. aqueous ethanol, optionally in the presence of a base, e.g. triethylamine.

Compounds of formula V may be prepared, for example, by the reaction of compounds of the general formula:

VI

-continued

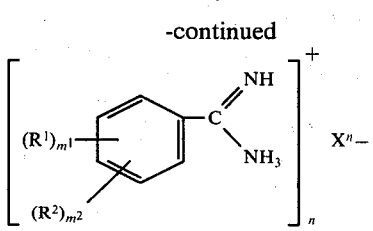

[wherein $R^1$, $R^2$, $m^1$ and $m^2$ are a hereinbefore defined, $X^{n-}$ represents the anion of a suitable acid, for example an inorganic acid (e.g. hydrochloric acid), or a strong organic acid (e.g. methanesulphonic or toluene-p-sulphonic acid), and $n$ is the basicity of that acid] with an alkyl α-oximinocyanoacetate, for example ethyl α-oximinocyanoacetate, in the presence of a lower alkoxide of an alkali metal in a lower alkanol, for example sodium ethoxide in ethanol.

Compounds of formula VI may be prepared by the action of acids of the general formula $H_nX$ (wherein X and n are as hereinbefore defined) on compounds of the general formula:

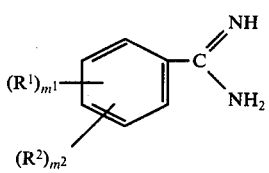

VII (wherein $R^1$, $R^2$, $m^1$ and $m^2$ are as hereinbefore defined), which may themselves be prepared, for example, by the reaction of alcoholic ammonia with compounds of the general formula:

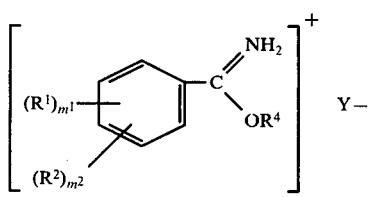

VIII (wherein $R^1$, $R^2$, $m^1$ and $m^2$ are as hereinbefore defined, $R^4$ represents an alkyl group containing from 1 to 6 carbon atoms, preferably methyl or ethyl, and $Y^-$ represents a suitable anion, for example a chloride, borofluoride or fluorosulphonate ion) at temperatures between, for example, 0° and 60° C.

Compounds of formula VIII, wherein $R^1$, $R^2$, $R^4$, $m^1$ and $m^2$ are as hereinbefore defined and $Y^-$ is a borofluoride or a fluorosulphonate ion, may be prepared by the reaction of the appropriate trialkyloxonium borofluoride and alkyl fluorosulphonate respectively [wherein the alkyl group(s) are groups $R^4$] with compounds of the general formula:

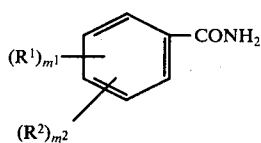

IX (wherein $R^1$, $R^2$, $m^1$ and $m^2$ are as hereinbefore defined) in a suitable solvent, for example anhydrous methylene chloride, preferably at or near the ambient temperature.

It will be readily appreciated by those skilled in the art that interconversions between different compounds of formula II are possible, for example as described in our aforementioned specifications.

As a further feature of the present invention, compounds, within general formula II, of the general formula:

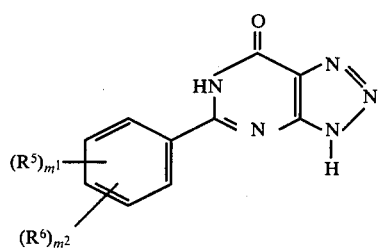

X (wherein $m^1$ and $m^2$ are as hereinbefore defined, $R^5$ represents an alkylsulphonyl group, and $R^6$ represents one or more identical or different substituents selected from halogen atoms and alkoxy, alkoxyalkoxy, phenoxy, aralkoxy, trifluoromethyl and methylenedioxy groups) may be prepared by oxidation of compounds of the general formula:

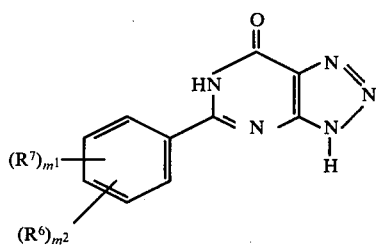

XI wherein $R^6$, $m^1$ and $m^2$ are as hereinbefore defined and $R^7$ represents an alkylthio or alkylsulphinyl group.

Compounds within general formula II of the general formula:

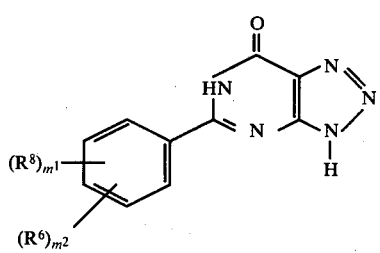

XII (wherein $R^6$, $m^1$ and $m^2$ are as hereinbefore defined and $R^8$ represents an alkylsulphinyl group) may be prepared by oxidation under mild conditions of a compound of the general formula:

XIII

-continued

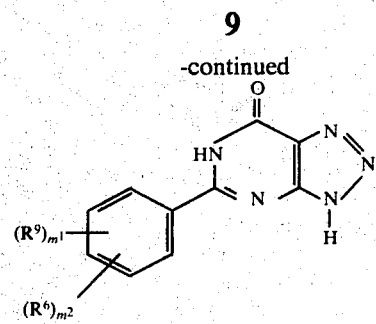

wherein $R^6$, $m^1$ and $m^2$ are as hereinbefoe defined and $R^9$ represents an alkylthio group.

Compounds of formula X, wherein $R^5$, $R^6 m^1$ and $m^2$ are as hereinbefore defined, may be prepared from compounds of formula XI, wherein $R^6$, $R^7$, $m^1$ and $m^2$ are as hereinbefore defined, by the action of potassium permanganate, preferably in the presence of an aqueous alkali metal hydroxide solution (e.g. sodium hydroxide) and at an elevated temperature (e.g. 60°–100° C.), or alternatively by the action of aqeuous hydrogen peroxide solution, preferably in the presence of a carboxylic acid (e.g. acetic acid) and optionally at an elevated temperature.

Compounds of formula XII, wherein $R^6$, $R^8$, $m^1$ and $m^2$ are as hereinbefore defined, may be prepared from compounds of formula XIII, wherein $R^6$, $R^9$, $m^1$ and $m^2$ are as hereinbefore defined, by the action of sodium periodate, preferably in aqueous conditions and generally at or near the ambient temperature.

As a further feature of the present invention, compounds, within general formula II, of the general formula:

XIV

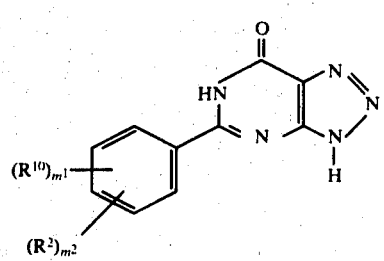

(wherein $R^6$, $m^1$ and $m^2$ are as hereinbefore and $R^{10}$ represents and alkoxycarbonyl group) may be prepared by the oxidation of compounds, within general formula I, of the general formula:

XV

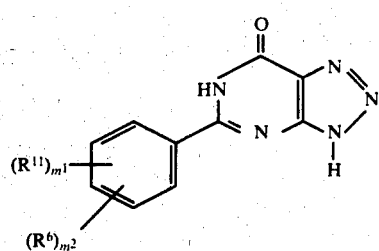

(wherein $R^6$, $m^1$ and $m^2$ are as hereinbefore defined and $R^{11}$ represents a lower alkyl group, preferably a methyl group) to form carboxylic acids of the general formula:

XVI

-continued

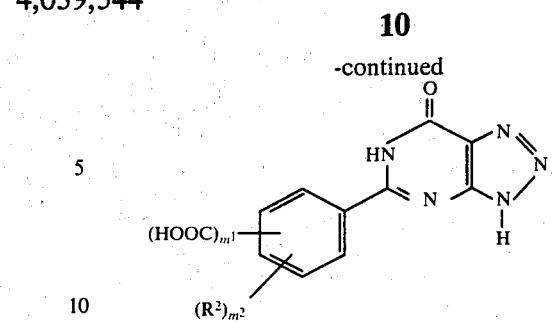

(wherein $R^6$, $m^1$ and $m^2$ are as hereinbefore defined), followed by esterification.

The oxidation and esterification reactions may be carried out by the application or adaptation of methods known per se without affecting the rest of the molecule. By the term "methods known per se" as used in this specification is meant methods heretofore used or described in the chemical literature.

For example, the oxidation of compounds of formula XV to form carboxylic acids of formula XVI may be carried out by the action of an alkali metal permanganate (e.g. sodium permanganate or potassium permanganate), preferably in the presence of an aqueous alkali metal hydroxide (e.g. sodium hydroxide) and at an elevated temperature (e.g. 60°–100° C.).

The esterification of carboxylic acids of formula XVI to form esters of formula II may be carried out, for example, by the action of the appropriate alcohol (which, when liquid, can act as the solvent medium), in the presence of an inorganic acid, for example dry hydrogen chloride, preferably at an elevated temperature (e.g. 60°–100° C.).

The present invention includes pharmaceutically acceptable salts of compounds of general formula II with pharmaceutically acceptable bases. By the term "pharmaceutically acceptable salts" is meant salts the cations of which are relatively innocuous to the animal organism when used in therapeutic doses so that the beneficial pharmacological properties of the parent compounds are not vitiated by side effects ascribable to those cations. Suitable salts include the alkali metal, e.g. sodium and potassium, and ammonium salts and salts of amines known in the art to be pharmaceutically acceptable, e.g. ethylene diamine, choline, diethanolamine, triethanolamine, octadecylamine and 1-(3,4-dihydroxyphenyl)-2-isopropylaminoethanol.

Pharmaceutically acceptable salts may be prepared by the reaction together of stoichiometric quantities of a compound of general formula II and the appropriate base, that is to say, a base as described immediately hereinbefore, for example at an elevated temperature, with or without an appropriate solvent, preferably followed by recrystallisation from an appropriate solvent, for example a hydroxylic solvent, e.g. an alkanol, of the salt so formed.

The following Examples illustrate the preparation of the new compounds of the present invention.

EXAMPLE 1

Dry hydrogen chloride gas was passed through a suspension of 8-aza-2-(5-carboxy-2-propoxyphenyl)purin-6-one (3 g.) in dry ethanol (60 ml.) under reflux for 3 hours. The mixture was kept under reflux for a further 20 hours and then the ethanol was removed in vacuo to give a semi-solid material which was then dissolved in aqueous ammonia solution (2N; 50 ml.). The resulting cloudy solution was washed with diethyl ether (50 ml.), treated with charcoal and filtered, and then acidified with glacial acetic acid. The solid which separated was recrystallised from ethanol, to give 8-aza-2-(5-ethoxycarbonyl-2-propoxyphenyl)purin-6-one (0.4 g.), m.p. 223° – 225° C.

By proceeding in a similar manner, but replacing the ethanol used by the apropriate quantities of methanol and butanol respectively, there were prepared: 8-aza-2-(5-methoxycarbonyl-2-propoxyphenyl)purin-6-one, m.p. 270° – 272° C. (with decomposition; recrystallised from 2-ethoxyethanol), and 8-aza-2-(5-butoxycarbonyl-2-propoxyphenyl)purin-6-one, m.p. 174° – 176° C. (recrystallised from aqueous acetone).

The 8-aza-2-(5-carboxy-2-propoxyphenyl)purin-6-one, used as a starting material in the above preparations, was prepared as follows:

A suspension of 8-aza-2-(5-methyl-2-propoxyphenyl)-purin-6-one (2.85 g.; prepared as described in Example 31 of British patent specification No. 1338235) in water (80 ml.) was treated with sodium hydroxide (1.0 g.). Potassium permanganate (6.3 g.) was then added to the resulting solution, and the mixture was stirred and heated at reflux for 150 minutes. The hot mixture was filtered through diatomaceous earth to remove manganese dioxide and the filtrate was acidified with concentrated hydrochloric acid. The solid precipitated was then dissolved in hot aqueous ammonia solution (2N) and then acidified again with concentrated hydrochloric acid. The resulting hot suspension was then filtered and the white solid formed was washed with water. The solid was treated with ethanol (50 ml.) and the resulting suspension was brought to reflux and the 8-aza-2-(5-carboxy-2-propoxyphenyl)purin-6-one (1.8 g.), m.p. 271° – 272° C. (with decomposition), was filtered off from the hot mixture.

EXAMPLE 2

A solution of concentrated hydrochloric acid (200 ml.) in water (200 ml.) was stirred and maintained at 0° C. and treated with sodium nitrite (9.0 g.). The resulting solution was stirred and maintained at 0° C. and treated with 4,5-diamino-2-(2-propoxy-5-propylsulphonylphenyl)pyrimid-6-one (15.0 g.) during 30 minutes, followed by a further quantity of sodium nitrite (9.0 g.). The mixture was then stirred at 0° C. for 2 hours and then at room temperature for 18 hours and then the solid was filtered off, washed with water, sucked dry, and recrystallised from ethanol, to give 8-aza-2-(2-propoxy-5-propylsulphonylphenyl)purin-6-one (12.0 g.), m.p. 267° – 268° C. (with decomposition).

By proceeding in a similar manner, but replacing the 4,5-diamino-2-(2-propoxy-5-propylsulphonylphenyl)-pyrimid-6-one used as starting material by the appropriate quantities of 4,5-diamino-2-(2-propoxy-5-methylsulphonylphenyl)pyrimid-6-one and 4,5-diamino-2-(2-propoxy-5-t-butylsulphonylphenyl)-pyramid-6-one, there were prepared 8-aza-2-(2-propoxy-5-methylsulphonylphenyl)purin-6-one, m.p. 262° – 263° C. (with decomposition), and 8-aza-2-(2-propoxy-5-t-butylsulphonylphenyl)purin-6-one, m.p. 253.5° – 255° C., respectively.

EXAMPLE 3

A solution of sodium nitrite (3.75 g.) in water (7 ml.) was added to a mixture of glacial acetic acid (65 ml.) and water (3 ml.) at 8° C. at such a rate that the temperature did not exceed 10° C. The solution was cooled to 5° C. and treated with fresh 4,5-diamino-2-(2-propoxy-5-t-butylthiophenyl)pyrimid-6-one [the damp material prepared as described hereafter in Reference Example 9 from 6.5 g. of 4-amino-5-nitroso-2-propoxy-5-t-butylthiophenyl)pyrimid-6-one] portionwise during 30 minutes. The mixture was then stirred at 5° – 10° C. for 1 hour and then at room temperature for 18 hours. The mixture was diluted with three times its volume of water and a pink solid was obtained. This solid was dissolved in an aqueous solution of ammonia (2N; 100 ml.), the solution was treated with charcoal at about 80° C., filtered hot, and the resulting colourless solution was acidified with concentrated hydrochloric acid. The resulting precipitate was filtered off, to give 8-aza-2-(2-propoxy-5-t-butylthiophenyl)purin-6-one (4.0 g.), m.p. 186.5° – 189° C.

EXAMPLE 4

8-Aza-2-(2-propoxy-5-t-butylthiophenyl)purin-6-one (2.5 g.; prepared as described in Example 3) was dissolved in a solution of sodium hydroxide (1.0 g.) in water (80 ml.) at 80° C. and treated with potassium permanganate (3.6 g.). The mixture was heated and stirred on the steam bath for 2 hours. The excess of potassium permanganate was then decomposed by the addition of ethanol, and the hot mixture was filtered through diatomaceous earth to remove manganese dioxide. Acidification of the filtrate with hydrochloric acid gave a white solid, which was filtered off and recrystallised from ethanol, to give 8-aza-2-(2-propoxy-5-t-butylsulphonylphenyl)purin-6-one (1.6 g.), m.p. 253.5° – 255.5° C. (with decomposition), identical with that prepared as described in Example 2.

EXAMPLE 5

A mixture of 8-aza-2-(2-propoxy-5-t-butylthiophenyl)purin-6-one (0.36 g.; prepared as described in Example 3), sodium bicarbonate (0.25 g.) and water (20 ml.) was heated gently until complete solution occurred. The solution was cooled to room temperature and treated with sodium periodate (0.23 g.), and the mixture was stirred for 4 hours, after which time thin layer chromatography [on silica gel, using as eluant a mixture of chloroform, methanol and 99% w/w formic acid (86:10:4 by volume)] indicated that only a small trace of the starting material remained. The mixture was then treated with sodium sulphite (1.0 g.) and stirring was continued for 5 minutes. The mixture was acidified with concentrated hydrochloric acid and cooled, and the resulting white solid (0.25 g.) was filtered off and recrystallised from aqueous methanol, to give 8-aza-2-(2-propoxy-5-t-butylsulphinylphenyl)purin-6-one (0.2 g.), m.p. 195° – 196° C. (with decomposition).

EXAMPLE 6

By proceeding as hereinbefore described in Example 2, but replacing the 4,5-diamino-2-(2-propoxy-5-propylsulphonylphenyl)pyrimid-6-one used as starting material by the appropriate quantities of 4,5-diamino-2-(2-propoxy-5-isopropylsulphonylphenyl)pyrimid-6-one and 4,5-diamino-2-(2-propoxy-5-isobutylsulphonylphenyl)pyrimid-6-one, there were prepared 8-aza-2-(2-propoxy-5-isopropylsulphonylphenyl)-purin-6-one, m.p. 211° – 212° C., and 8-aza-2-(2-propoxy-5-isobutylsulphonylphenyl)purin-6-one, m.p. 263° – 265° C., respectively.

EXAMPLE 7

A mixture of 8-aza-2-(2-propoxy-5-propylsulphonyl-phenyl)purin-6-one (0.37 g.; prepared as described in Example 2) and triethanolamine (0.16 g.) in dry ethanol (15 ml.) was heated at reflux until solution occurred. The crystalline mass formed on cooling was filtered off, washed with dry ethanol and recrystallised from dry ethanol to give the triethanolamine salt of 8-aza-2-(2-propoxy-5-propylsulphonylphenyl)purin-6-one (0.3 g.).

In a similar manner there was prepared the triethanolamine salt of 8-aza-2-(5-butoxycarbonyl-2-propoxy-phenyl)purin-6-one (see Example 1).

The following Reference Examples illustrate the preparation of the 4,5-diamino-2-phenylpyrimid-6-one derivatives used as starting materials in the above Examples.

REFERENCE EXAMPLE 1

Chlorosulphonic acid (200 ml.), cooled to 10° C., was treated with 2-propoxybenzamide (60 g.) in aliquots with stirring during 45 minutes. When complete solution had occurred, the solution was allowed to stand at room temperature for 24 hours. The resulting yellow-brown solution was then added dropwise, with stirring, to ice (1.5 kg.), keeping the temperature at or below 0° C. The precipitated solid was filtered off, washed with ice-cold water, and sucked dry. The solid was then dissolved in dichloromethane (approximately 2 liters), any water still present was separated off, and the organic layer was dried over calcium chloride and then over magnesium sulphate. Most of the dichloromethane was removed in vacuo, the low volume residue was treated with petroleum ether (b.p. 40° – 60° C.) and the precipitated solid was filtered off, to give crude 5-chlorosulphonyl-2-propoxybenzamide (81 g.), m.p. 122° – 129° C.

REFERENCE EXAMPLE 2

Finely powdered 5-chlorosulphonyl-2-propoxybenzamide (3.0 g.; prepared from the product described in Reference Example 1) was added to a mixture of concentrated sulphuric acid (12 ml.), water (25 ml.) and ethanol (25 ml.) at −20° C. The mixture was allowed to warm to −5° C. with stirring, and then powdered zinc (6 g.) was added at such a rate that the temperature did not exceed 0° C. After stirring at between −5° C. for 90 minutes, then at room temperature for 90 minutes, water (50 ml.) was added and the resulting dark suspension was finally heated to boiling for approximately 75 minutes, distilling off a mixture of ethanol and water. When the temperature at the distillation head reached 96° C., distillation was stopped and the residue was cooled to room temperature. The precipitated solid was then extracted with chloroform (3 × 25 ml.). The chloroform extract was filtered to remove any remaining zinc, washed with water (2 × 10 ml.) and dried over sodium sulphate. Removal of the solvent gave an off-white solid which was recrystallised from ethanol at −30° C., to give slightly impure 2-propoxy-5-mercap-tobenzamide (1.3 g.). This material was sufficiently pure for use in the next stage. Purer 2-propoxy-5-mercap-tobenzamide (0.8 g.), m.p. 108° – 111° C., was obtained by further recrystallisation from a small amount of ethanol (only cooling to 0° C. instead of to −30° C.).

REFERENCE EXAMPLE 3 t-Butanol (16 g.) was added to an aqueous sulphuric acid solution (200 ml.; containing 75% w/w sulphuric acid) cooled in ice-water. The mixture was stirred until all the t-butanol had dissolved, and then 2-propoxy-5-mercaptobenzamide (20 g.; prepared as described in Reference Example 2) was added in small portions with stirring during 15 minutes. After all the solid had dissolved the mixture was allowed to warm up to room temperature and kept at that temperature for 15 minutes. The solution was diluted with water (600 ml.), and the precipitated solid was filtered off and dissolved in chloroform (200 ml.). The chloroform solution was then washed with aqueous sodium hydroxide solution (2N; 40 ml.) and then with water (3 × 20 ml.), and dried over sodium sulphate. The solvent was removed in vacuo and the residue was recrystallised from aqueous ethanol, to give 5-t-butylthio-2-propoxybenzamide (15 g.), m.p. 135.5° – 137.5° C.

REFERENCE EXAMPLE 4

An intimate mixture of crude 5-chlorosulphonyl-2-propoxybenzamide (2.77 g.; prepared as described in Reference Example 1) and sodium bicarbonate (1.5 g.) was added in small portions during 30 minutes to a stirred solution of sodium sulphite (2.52 g.) and sodium bicarbonate (0.2 g.) in water (25 ml.) at 70° –80° C. The mixture was then stirred for a further 30 minutes and then cooled to 0° C. Concentrated hydrochloric acid was then added until the pH of the mixture reached pH 1, and the resulting precipitate was filtered off and washed with ice-cold water. This solid was then dissolved in a solution of sodium carbonate (0.58 g.) in water (20 ml.). The solution was treated with ethanol (20 ml.) and then with propyl bromide (1.35 g.). The mixture was stirred and heated gently at reflux for 24 hours, then cooled and diluted with an equal volume of water and left to stand. The resulting crystalline precipitate was filtered off and recrystallised from ethanol, to give 2-propoxy-5-propylsulphonylbenzamide (1.85 g.), m.p. 173° – 175° C.

By proceeding in a similar manner, but replacing the propyl bromide used as a starting material by the appropriate quantity of methyl iodide, there was prepared 5-methylsulphonyl-2-propoxybenzamide, m.p. 168° – 170° C. (recrystallised from water).

REFERENCE EXAMPLE 5

5-t-Butylthio-2-propoxybenzamide (4.0 g.; prepared as described in Reference Example 3), was dissolved in glacial acetic acid (24 ml.) and treated with an aqueous solution of hydrogen peroxide (30% w/w; 12 ml.). The mixture was heated in an open flask on the steam bath for 4 hours. The mixture was then diluted with water and the resulting solid was filtered off and recrystallised from acetone, to give 5-t-butylsulphonyl-2-propoxyben-zamide (2.8 g.), m.p. 215° – 218° C.

REFERENCE EXAMPLE 6

2-Propoxy-5-propylsulphonylbenzamide (20 g.; prepared as described in Reference Example 4) was suspended in dry methylene chloride (300 ml.) and treated with methyl fluorosulphonate (10 g.). The mixture was stirred for 24 hours. The methylene chloride was then removed from the resulting solution in vacuo and then a solution of ammonia in dry methanol (saturated at 0° C.; 200 ml.) was added. The solution thus obtained was left standing in a sealed flask at room temperature for 96 hours and was then concentrated in vacuo. The resulting oil was dissolved in methylene chloride (200 ml.), treated with water (100 ml.), and the mixture was cooled to 0° C. An aqueous sodium hydroxide solution (50% w/w; 50 ml.) was then added dropwise with stirring during 10 minutes, keeping the temperature between 0° and 10° C. The mixture was stirred for a further 5 minutes and the organic layer was then separated, washed with water (20 ml.), and dried over anhydrous potassium carbonate. Removal of the solvent gave a solid, which was dissolved in a minimum quantity of dry methylene chloride and was then treated with a slight excess of a dry saturated solution of hydrogen chloride in diethyl ether. Dry diethyl ether was then added, causing the formation of an oily solid which, on scratching, completely solidified. The solid was redissolved in a minumum of dry methylene chloride and the solution was treated with diethyl ether. The resulting solid was filtered off, to give 2-propoxy-5-propylsulphonylbenzamidine hydrochloride (19 g.), m.p. 162° – 164° C. (with decomposition).

By proceeding in a similar manner, but replacing the 2-propoxy-5-propylsulphonylbenzamide used as starting material by the appropriate quantities of 5-methylsulphonyl-2-propoxybenzamide, 5-t-butylsulphonyl-2-propoxybenzamide and 5-t-butylthio-2-propoxybenzamide, there were prepared 5-methylsulphonyl-2-propoxybenzamidine hydrochloride, m.p. 170°–173° C., 5-t-butylsulphonyl-2-propoxybenzamidine hydrochloride, m.p. 166°–169° C., and 5-butylthio-2-propoxybenzamidine hydrochloride (in the form of a clear gum), respectively.

REFERENCE EXAMPLE 7

By proceeding in the manner described in Example 1 of British patent specification No. 1338235, but using as starting materials the following salts of benzamidine derivatives and operating at reaction temperatures as indicated:

2-propoxy-5-propylsulphonylbenzamidine hydrochloride (room temperature),
5-methylsulphonyl-2-propoxybenzamidine hydrochloride (room temperature),
5-t-butylsulphonyl-2-propoxybenzamidine hydrochloride (room temperature), and
5-t-butylthio-2-propoxybenzamidine hydrochloride (reflux temperature), there were prepared
4-amino-5-nitroso-2-(2-propoxy-5-propylsulphonylphenyl)-pyrimid-6-one, m.p. 201°–204° C.,
4-amino-5-nitroso-2-(2-propoxy-5-methylsulphonylphenyl)-pyrimid-6-one, m.p. 243°–244° C. (with decomposition),
4-amino-5-nitroso-2-(2-propoxy-5-t-butylsulphonylphenyl)-pyrimid-6-one, m.p. 212°–213° C. (with decomposition), and 4-amino-=-nitroso-2-(2-propoxy-5-t-butylthiophenyl)pyrimid-6-one, m.p. 210°–212° C. (with decomposition), respectively.

REFERENCE EXAMPLE 8

By proceeding in the manner described in Example 1 of British patent specification No. 1338235, but using as starting materials the following nitroso-compounds:

4-amino-5-nitroso-2-(2-propoxy-5-propylsulphonylphenyl)-pyrimid-6-one,
4-amino-5-nitroso-2-(2-propoxy-5-methylsulphonylphenyl)-pyrimid-6-one, and
4-amino-5-nitroso-2-(2-propoxy-5-t-butylsulphonylphenyl)-pyrimid-6-one, respectively, there were prepared the following 4,5-diamino-2-phenylpyrimid-6-one derivatives:
4,5-diamino-2-(2-propoxy-5-propylsulphonylphenyl)-pyrimid-6-one, m.p. 228°–230° C. (with decomposition and previous darkening),
4,5-diamino-2-(2-propoxy-5-methylsulphonylphenyl)-pyrimid-6-one, m.p. 245°–248° C. (with decomposition and previous darkening), and
4,5-diamino-2-(2-propoxy-5-t-butylsulphonylphenyl)-pyrimid-6-one, m.p. 249°–252.5° C. (with decomposition and previous darkening), respectively.

REFERENCE EXAMPLE 9

4-Amino-5-nitroso-2-(2-propoxy-5-t-butylthiophenyl)-pyrimid-6-one (6.5 g.) (see Reference Example 7) was dissolved in boiling ethanol (150 ml.), and the solution was added all at once to a solution of sodium dithionite (26 g.) in water (150 ml.) at 80° C. The mixture immediately turned yellow. After 2 minutes, the mixture was cooled to room temperature and diluted with water (700 ml.), and then it was left to stand in an ice bath for 1 hour. The solid formed [4,5-diamino-2-(2-propoxy-5-t-butylthiophenyl)-pyrimid-6-one] was filtered off and washed with water. This material was used immediately for the next stage of the synthesis, because darkening occurred on standing.

REFERENCE EXAMPLE 10

An intimate mixture of crude 5-chlorosulphonyl-2-propoxybenzamide (2.77 g.; prepared as described in Reference Example 1) and sodium bicarbonate (1.5 g.) was added in small portions during 30 minutes to a stirred solution of sodium sulphite (2.52 g.) and sodium bicarbonate (0.2 g.) in water (25 ml.) at 70°–80° C. The mixture was then stirred for a further 30 minutes and was then cooled to 0° C. Concentrated hydrochloric acid was then added until the pH of the mixture reached pH 1, and the resulting precipitate was filtered off and washed with ice-cold water. This solid was added to a solution of sodium ethoxide [prepared from sodium (0.25 g.) and ethanol (20 ml.)] and the mixture was heated on the steam bath for 30 minutes. After removal of the solvent in vacuo, the resulting sodium salt was dried by removing any remaining water as its azeotrope with toluene. The dry salt was then added to dry sulpholane (30 ml.) and isopropyl bromide (5 ml.) and the mixture was heated at 80° C., with stirring, for 10 hours. The resulting solution was added to ice-water (400 ml.). The orange precipitate that formed was recrystallised from ethanol, with the aid of decolourising charcoal, to give 5-isopropylsulphonyl-2-propoxybenzamide (0.75 g.), m.p. 194°–195° C.

By proceeding in a similar manner, but replacing the isopropyl bromide used as a starting material by the appropriate quantity of isobutyl iodide, there was prepared 5-isobutylsulphonyl-2-propoxybenzamide, m.p. 177°–178° C.

REFERENCE EXAMPLE 11

By proceeding as hereinbefore described in Reference Example 6, but replacing the 2-propoxy-5-propylsulphonylbenzamide used as starting material by the appropriate quantities of 5-isopropylsulphonyl-2-propoxybenzamide and 5-isobutylsulphonyl-2-propoxybenzamide, there were prepared 5-isopropylsulphonyl-2-propoxybenzamidine hydrochloride, m.p. 175°–178° C., and (omitting the procedure of dissolving the crude base in methylene chloride and treatment with hydrogen chloride and diethyl ether and instead recrystallising the crude base from toluene) 5-isobutylsulphonyl-2-propoxybenzamidine, m.p. 125°–126° C., respectively.

REFERENCE EXAMPLE 12

By proceeding as hereinbefore described in Reference Example 7, but using as starting materials 5-isopropylsulphonyl-2-propoxybenzamidine hydrochloride and 5-isobutylsulphonyl-2-propoxybenzamidine (see Reference Example 11), there were prepared 4-amino-5-nitroso-2-(2-propoxy-5-isopropylsulphonylphenyl)-pyrimid-6-one, m.p. 200°–202° C., and 4-amino-5-nitroso-2-(2-propoxy-5-isobutylsulphonylphenyl)-pyrimid-6-one, m.p. 215°–217° C., respectively.

REFERENCE EXAMPLE 13

By proceeding as hereinbefore described in Reference Example 8, but using as starting materials 4-amino-5-nitroso-2-(2-propoxy-5-isopropylsulphonylphenyl)-pyrimid-6-one and 4-amino-5-nitroso-2-(2-propoxy-5-isobutylsulphonylphenyl)pyrimid-6-one (see Reference Exmple 12), there were prepared 4,5-diamino-2-(2-propoxy-5-isopropylsulphonylphenyl)pyrimid-6-one, m.p. 219°–220° C. (with darkening and decomposition), and 4,5-diamino-2-(2-propoxy-5-isobutylsulphonylphenyl)pyrimid-6-one, m.p. 217°–218° C. (with darkening and decomposition), respectively.

The present invention includes within its scope pharmaceutical compositions which comprise one or more compounds of general formula II, or a pharmaceutically acceptable salt thereof, in association with a pharmaceutical carrier or coating. In clinical practice the compounds of the present invention will normally be administered orally, sub-lingually, nasally, rectally or parenterally.

Such compositions, their preparation, and their use are analogous to those described in our aforementioned Specifications with reference to compositions containing compounds of formula I.

The following Examples illustrate pharmaceutical compositions according to the present invention.

EXAMPLE 8

Micromilled triethanolamine salt of 8-aza-2-(5-butoxycarbonyl-2-propoxyphenyl)purin-6-one (100 mg.) and oleyl alcohol (200 mg.) were placed in a polyvinyl chloride-coated glass bottle (20 ml. capacity) and filled with a mixture of dichlorodifluoromethane and dichlorotetrafluoroethane to give a total volume of 7.2 ml. The bottle was sealed with a metered valve (with dip tube) delivering 0.1 ml. doses. Each puff (generated from 0.1 ml. of solution) of aerosol released from the pressurized pack thus obtained contained 1 mg. of 8-aza-2-(5-butoxycarbonyl-2-propoxyphenyl)purin-6-one [in terms of the free 8-aza-2-(5-butoxycarbonyl-2-propoxyphenyl)-purin-6-one].

EXAMPLE 9

Micromilled triethanolamine salt of 8-aza-2-(2-propoxy-5-propylsulphonylphenyl)purin-6-one (100 mg.) and oleyl alcohol (200 mg.) were placed in a polyvinyl chloride-coated glass bottle (20 ml. capacity) and filled with a mixture of dichlorodifluoromethane and dichlorotetrafluoroethane to give a total volume of 7.2 ml. The bottle was sealed with a metered valve (with dip tube) delivering 0.1 ml. doses. Each puff (generated from 0.1 ml. of solution) of aerosol released from the pressurized pack thus obtained contained 1 mg. of 8-aza-2-(2-propoxy-5-propylsulphonylphenyl)purin-6-one [in terms of the free 8-aza-2-(2-propoxy-5-propylsulphonylphenyl)purin-6-one].

Similar compositions were prepared from pharmaceutically acceptable salts of other compounds of formula II.

We claim:

1. An 8-azapurin-6-one of the formula:

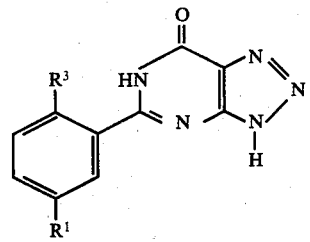

wherein $R^3$ is straight- or branched-chain alkoxy of from 1 to 4 carbon atoms and $R^1$ is alkylthio of 1 to 6 carbon atoms, alkylsulphinyl of 1 to 6 carbon atoms, alkylsulphonyl of 1 to 6 carbon atoms, or alkoxycarbonyl of 2 to 7 carbon atoms, and pharmaceutically acceptable salts thereof.

2. An 8-azapurin-6-one according to claim 1 which is 8-aza-2-(5-ethoxycarbonyl-2-propoxyphenyl)purin-6-one or a pharmaceutically acceptable salt thereof.

3. An 8-azapurin-6-one according to claim 1 which is 8-aza-2-(5-methoxycarbonyl-2-propoxyphenyl)-purin-6-one or a pharmaceutically acceptable salt thereof.

4. An 8-azapurin-6-one according to claim 1 which is 8-aza-2-(5-butoxycarbonyl)-2-propoxyphenyl)-purin-6-one or a pharmaceutically acceptable salt thereof.

5. An 8-azapurin-6-one according to claim 1 which is 8-aza-2-(2-propoxy-5-propylsulphonylphenyl)-purin-6-one or a pharmaceutically acceptable salt thereof.

6. An 8-azapurin-6-one according to claim 1 which is 8-aza-2-(2-propoxy-5-methylsulphonylphenyl)-purin-6-one or a pharmaceutically acceptable salt thereof.

7. An 8-azapurin-6-one according to claim 1 which is 8-aza-2-(2-propoxy-5-t-butylsulphonylphenyl)-purin-6-one or a pharmaceutically acceptable salt thereof.

8. An 8-azapurin-6-one according to claim 1 which is 8-aza-2-(2-propoxy-5-t-butylthiophenyl)-purin-6-one or a pharmaceutically acceptable salt thereof.

9. An 8-azapurin-6-one according to claim 1 which is 8-aza-2-(2-propoxy-5-t-butylsulphinylphenyl)-purin-6-one or a pharmaceutically acceptable salt thereof.

10. An 8-azapurin-6-one according to claim 1 which is 8-aza-2-(2-propoxy-5-isopropylsulphonylphenyl)-purin-6-one or a pharmaceutically acceptable salt thereof.

11. An 8-azapurin-6-one according to claim 1 which is 8-aza-2-(2-propoxy-5-isobutylsulphonylphenyl)-purin-6-one or a pharmaceutically acceptable salt thereof.

12. The 8-azapurin-6-one according to claim 1 which is the triethanolamine salt of 8-aza-2-(2-propoxy-5-propylsulphonylphenyl)purin-6-one.

13. The 8-azapurin-6-one according to claim 1 which is the triethanolamine salt of 8-aza-2-(5-butoxy-carbonyl-2-propoxyphenyl)purin-6-one.

* * * * *